(12) United States Patent
Oita

(10) Patent No.: US 6,329,011 B1
(45) Date of Patent: Dec. 11, 2001

(54) ANTIMICROBIAL AGENT AGAINST ACID-RESISTANT AND HEAT-RESISTANT BACTERIA

(75) Inventor: Shigeru Oita, Zentsuji (JP)

(73) Assignees: Director General of Shikoku National Agricultural Experiment Station; Ministry of Agriculture, Forestry and Fisheries, both of Zentsuji (JP)

( * ) Notice: Subject to any disclaimer, the term of this patent is extended or adjusted under 35 U.S.C. 154(b) by 0 days.

(21) Appl. No.: 09/680,403

(22) Filed: Oct. 5, 2000

(30) Foreign Application Priority Data

Jul. 26, 2000 (JP) ................................. 12-224738

(51) Int. Cl.[7] .......................... A61K 38/00; C07K 14/00; A23L 2/02
(52) U.S. Cl. ............................ 426/599; 514/12; 530/324; 426/599; 426/656; 426/335; 426/268; 435/252; 435/252.1; 435/252.31; 435/252.5; 435/832; 435/833; 435/834; 435/835; 435/836; 435/837; 435/838; 435/839
(58) Field of Search .......................... 514/2, 12; 530/324; 426/268, 321, 656, 335, 599; 435/252.5, 252, 252.1, 252.31, 832, 833, 834, 835, 836, 837, 838, 839

(56) References Cited

PUBLICATIONS

Florack et al. Thionins: properties, possible biological roles and mechanisms of action. Plant Molecular Biology 26, 25–37 (1994).*

Molina et al. Inhibition of bacterial and fungal plant pathogens by thionins of types I and II. Plant Science 92, 169–177 (1993).*

* cited by examiner

Primary Examiner—Christopher S. F. Low
Assistant Examiner—Chih-Min Kam
(74) Attorney, Agent, or Firm—Oblon, Spivak, McClelland, Maier & Neustadt, P.C.

(57) ABSTRACT

An antimicrobial agent with a high degree of safety is provided, which is derived from a natural product and can exhibit growth-inhibitory activity against acid-resistant and heat-resistant bacteria such as *Alicyclobacillus acidoterrestris,* which is resistant against pasteurization and causes spoilage of fruit juice. The antimicrobial agent against acid-resistant and heat-resistant bacteria contains as an effective ingredient alpha-type thionin and/or beta-type thionin. A preservative for fruit juice is also provided, which contains as an effective ingredient the alpha-type thionin and/or beta-type thionin.

15 Claims, 1 Drawing Sheet

ANTIMICROBIAL AGENT AGAINST ACID-RESISTANT AND HEAT-RESISTANT BACTERIA

FIELD OF THE INVENTION

The present invention relates to an antimicrobial agent against acid-resistant and heat-resistant bacteria, and more specifically, to an antimicrobial agent, which contains as an effective ingredient a safe peptide derived from a natural product, against acid-resistant and heat-resistant bacteria such as *Alicyclobacillus acidoterrestris*.

BACKGROUND OF THE INVENTION

As typical bacteria, which exhibit acid resistance in combination with heat resistance, there are known *Alicyclobacillus acidoterrestris, Alicyclobacillus acidocaldarius*, etc. The spores of these bacteria possess resistance against the normally employed pasteurization method for fruit juice. Therefore, in recent years, the spoilage of fruit juice caused by *Alicyclobacillus acidoterrestris* has been a serious problem throughout the world.

In order to suppress growth of the bacterium in fruit juice, it is effective to add a synthetic preservative such as benzoic acid. However, there is now strongly demanded a material with an enhanced degree of safety, which is derived from a natural product but not from a synthetic product.

As an antimicrobial agent, which is derived from a natural product and is effective against the bacterium, there has been reported only nisin, which is a peptide derived from lactic acid bacterium (International Journal of Food Science and Technology, vol. 34, pp. 81 to 85, 1999). However, nisin contains a special type of amino acids such as dehydroalanine.

Consequently, for the preservation and storage of fruit juice, there is demanded an antimicrobial agent, which is derived from a natural product and is effective at lower concentration, against acid-resistant and heat-resistant bacteria such as *Alicyclobacillus acidoterrestris*.

The inventor of the present invention has studied characteristics of alpha-type thionin and beta-type thionin, which are peptides derived from wheat and barley. To the best of the inventor's knowledge, no one has reported any antimicrobial activity of thionins against *Alicyclobacillus acidoterrestris*, which is an acid-resistant and heat-resistant bacteria, while its antimicrobial activity against phytopathogenic fungi has previously been known (Plant Science, vol. 92, pp. 169 to 177, 1993). In addition, such thionins do not contain any special amino acid at all, unlike the above-mentioned nisin derived from lactic acid bacteria.

SUMMARY OF THE INVENTION

An object of the present invention is to provide an antimicrobial agent with an enhanced degree of safety, which is derived from a natural product and exhibits growth-inhibitory activity against *Alicyclobacillus acidoterrestris*, which has acid-resistance and heat-resistance and causes spoilage of fruit juice. Another object of the present invention is to provide a preservative for fruit juice, which comprises the antimicrobial agent described above.

In order to attain the above-mentioned objects, the inventor of the present invention has conducted intensive screening of antimicrobial substances against *Alicyclobacillus acidoterrestris* from various agricultural crops, with the result that they found that alpha-type thionin and beta-type thionin, which are peptides of wheat and barley, exhibit growth-inhibitory activity against this bacteria. Thus, the inventor of the present invention has completed the present invention based on this finding.

Briefly, the present invention relates to an antimicrobial agent against acid-resistant and heat-resistant bacteria, characterized in that the antimicrobial agent contains as an effective ingredient alpha-type thionin and/or beta-type thionin.

Further, the present invention relates to a preservative for fruit juice, characterized in that the preservative contains as an effective ingredient alpha-type thionin and/or beta-type thionin.

DETAILED DESCRIPTION OF THE INVENTION

Figure 1A:
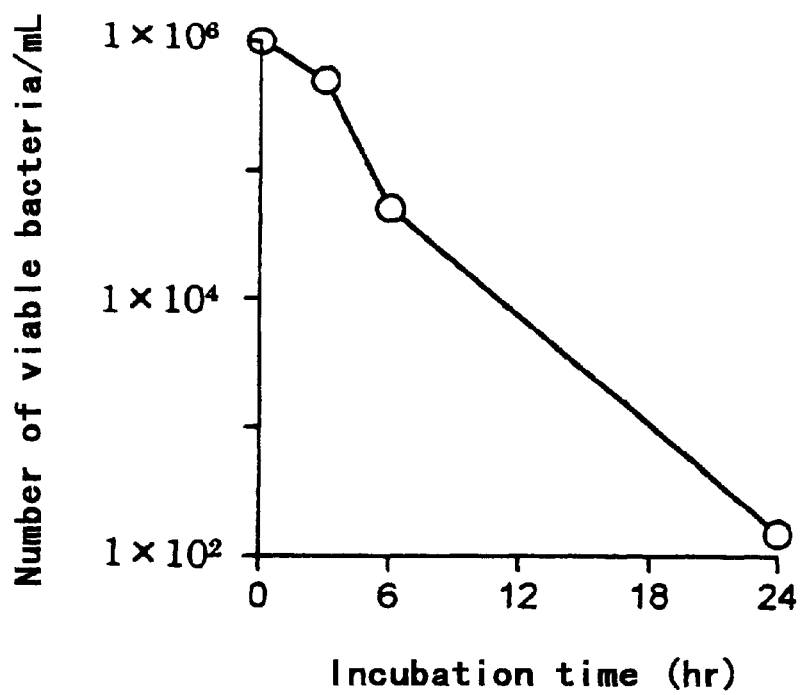
FIGS. 1A and 1B show changes with a lapse of time in number of viable bacteria of *Alicyclobacillus acidoterrestris* in each of fruit juice with thionin added; in which FIGS. 1A and 1B indicate results obtained from orange juice and apple juice, respectively.

Thionins, which are usable in the present invention, can be obtained from flour of grains such as barley, wheat, oats and rye, through extraction with saline solution or acids such as hydrochloric acid, sulfuric acid and acetic acid, and in addition, can also be produced with use of recombinant microorganisms or plants containing thionin genes.

Both of alpha-type thionin and beta-type thionin are composed of about 45 amino acids and about 8 cysteine contained among them, and have the molecular structure characterized in that partial or every cysteine residues form cross-linking by the disulfide bonds. The values of pH in fruit juices are usually in the range of 3 to 4 and these thionins are not denatured even in such acidic condition.

Such thionins can be purified by concentrating an extract of barley or wheat through salting out with ammonium sulfate, etc., followed by high-performance liquid chromatography, but any mixture (crude purification products) produced in the course of such purification process, can similarly be used in the present invention, only in the case where they can exhibit the desired antimicrobial activity.

The process for extraction and purification of thionins from barley was for example described in Planta, vol. 176, pp. 221 to 229 (1988), and it is also possible to carry out extraction and purification from other varieties of wheat and barley in accordance with the process.

There have already been known the entire amino acid sequences of thionins produced from barley, wheat, and oats (Plant Molecular Biology, vol. 26, pp. 25 to 37, 1994) as well as the amino acid composition of thionin of rye (Journal of Agricultural and Food Chemistry, vol. 26, pp. 794 to 796, 1978). It is to be noted that depending upon the race of wheat and barley, there may exist variant peptides having one or several amino acid residues undergone replacement, addition or deletion as compared with the known amino acid composition and sequences, and such variant peptides are included in the thionins which are usable in the present invention, as long as they exhibit the objective antimicrobial activity.

In the case where thionin is used as an antimicrobial agent against acid-resistant and heat-resistant bacteria or as a preservative for fruit juice, thionin or crude thionin is desirably added to fruit juice to a final concentration ranging from 5 to 100 µg/mL in case of the purified alpha-type one or ranging from 10 to 100 µg/mL in case of the purified beta-type one, in order to suppress growth of acid-resistant and heat-resistant bacteria such as *Alicyclobacillus acidoterrestris*, in fruit juice.

Since thionin does not lose antimicrobial activity after being heated under acidic conditions at 100° C. for 10 min. (Agricultural and Biological Chemistry, vol. 34, pp. 1089 to 1094, 1970), the antimicrobial activity of thionin can be maintained even when thionin is added to fruit juice, followed by pasteurization.

From the fact that no report has yet been published on any thionin-resistant mutant microorganism, and that thionin is degraded rapidly by digestive enzymes such as trypsin (Journal of the Japanese Society for Food Science and Technology, vol. 47, pp. 423 to 429, 2000), its effect on the enterobacteria can be considered to be extremely minor. In addition, it has been reported that one oral administration of thionin to guinea pigs at a dose of 103 to 229 mg/kg body weight, followed by observation for 7 days, did not result in detection of any abnormalities (Cereal Chemistry, vol. 19, pp. 301 to 307, 1942).

According to the present invention, there is provided the antimicrobial agent with a high degree of safety, which contains thionin as an effective ingredient and is derived from a natural product. Furthermore, the present invention also provides the preservative for fruit juice, which contains thionin as an effective ingredient. Such the antimicrobial agent and preservative exhibit growth inhibition against acid-resistant and heat-resistant bacteria such as *Alicyclobacillus acidoterrestris*, which cause spoilage of fruit juice. In addition, thionin is not denatured even after being heated under acidic conditions, and therefore effective for prevention of spoilage of fruit juice. Aqueous solutions of thionins are clear and odorless, and consequently do not affect the flavor of fruit juice.

EXAMPLES

The present invention will be described in detail with reference to examples, but the present invention is not intended to limit thereto.

Production Example 1

Grains of hull-less barley (variety: "ICHIBAN-BOSHI") were milled and powdered by a cyclon mill, and 100 g of the powders were admixed with 300 mL of distilled water, followed by stirring for 1 hour at 4° C. and subjecting to centrifugation to remove the resultant supernatant.

Then, the precipitate was admixed with 200 mL of 1M aqueous sodium chloride solution, and the mixture was stirred for 2 hours at 4° C. and subjected to centrifugation. The resultant supernatant was subjected with ammonium sulfate (50 to 90% saturated), and the recovered precipitate was suspended in a phosphate buffer, followed by centrifugation. Thus obtained supernatant was subjected to high-performance liquid chromatography to obtain purified alpha-type thionin and beta-type thionin of barley. In high-performance liquid chromatography, Wakosil 5C4-200, 4.6 mmφ×250 mm (supplied by Wako Pure Chemicals Ind. of Japan) was employed as a column, and concentration-gradient elution was carried out with water (pH 2.1) containing 0.1% trifluoroacetic acid and 0→40% (0→40 min) acetonitrile at a flow rate of 0.5 mL/min. Then, the collected fractions were evaporated to dryness with a centrifugal evaporator, followed by an amino acid analysis and a mass spectrum analysis, thereby being identified as alpha-type thionin and beta-type thionin. There were yielded 37 mg of alpha-type thionin and 12 mg of beta-type thionin, respectively, in terms of 1 kg of powdered grains of "ICHIBAN-BOSHI".

Production Example 2

100 g of commercially available, soft wheat flour was admixed with 300 mL of 0.15 N hydrochloric acid, and the resultant mixture was stirred. The mixture was then settled for 30 minutes at 37° C. and stirred again, followed by centrifugation. The resultant supernatant was neutralized by dropwise adding 10 N of aqueous sodium hydroxide solution, and then centrifugation was conducted again.

The supernatant thus obtained was subjected with ammonium sulfate (50 to 90% saturated), and the recovered precipitate was suspended in a phosphate buffer. The supernatant separated out by centrifugation was subjected to high-performance liquid chromatography under the same conditions as in Production Example 1, to give purified alpha-type thionin of wheat.

The collected fractions were concentrated to dryness by a centrifugal evaporator, followed by amino acid analysis and mass spectrum analysis, thereby being identified as alpha-type thionin. There was yielded 40 mg of alpha-type thionin in terms of 1 kg of soft wheat flour.

Example 1

*Alicyclobacillus acidoterrestris* strain ATCC 49025 was inoculated into YPGB culture medium (0.25% of yeast extract, 0.5% of polypeptone, 0.1% of D-glucose, 0.05% of magnesium sulfate 7 hydrate ($MgSO_4 \cdot 7H_2O$), 0.2% of potassium chloride, pH 4), followed by cultivation for 2 days at 37° C., and the cultured broth was treated for 1 hour at 60° C. to prepare a spore suspension.

The YPGB culture media, which contained the specified amount of each different thionin as obtained in Production Examples 1 and 2, were inoculated individually with the spore suspension at a rate of $1 \times 10^4$ spores/mL, and cultivation was conducted for 2 days at 37° C., followed by investigation for bacterial growth.

The results are shown in Table 1. In the investigation, the bacterial growth was judged on the basis of visual observation of the degree of turbidity of each culture medium, but in the cases of 50 µg/mL and 100 µg/mL in thionin addition amount, the bacterial growth was judged through the plate culture of diluted broth, because the culture media became turbid by thionin. Further, in the case where thionins were not added as controls, bacterial growth was observed in every test group.

TABLE 1

| | Bacterial growth Thionin concentration (µg/mL) | | | | | | |
|---|---|---|---|---|---|---|---|
| Type of thionins | 100 | 50 | 20 | 10 | 5 | 2 | 1 |
| Alpha type of barley | − | − | − | − | − | + | + |
| Alpha type of wheat | − | − | − | − | − | + | + |
| Beta type of barley | − | − | − | − | + | + | + |

+: bacterial growth was observed
−: bacterial growth was not observed

Example 2

Figure 1B:
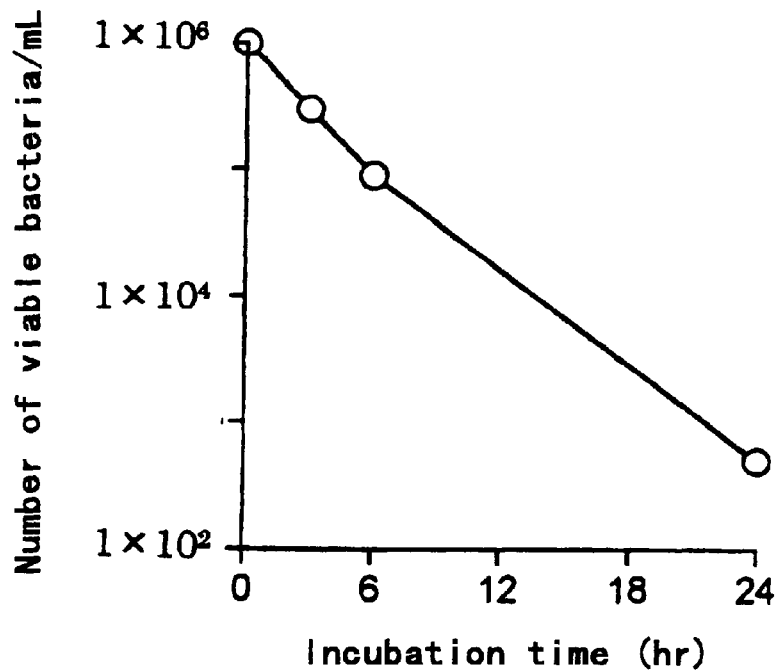

Commercially available, 100% orange juice and apple juice (pH value of 3.6 for both juice) were added with alpha-type thionin of barley at a final concentration of 20 μg/mL and then inoculated, at a rate of 1×10⁶ spores/mL, with the spore suspension of *Alicyclobacillus acidoterrestris* strain ATCC 49025 prepared in Example 1, respectively, and were incubated at 37° C. The number of viable bacteria in each juice was counted with a lapse of time though the dilution plate culture (for 2 days at 37° C.) in a potato dextrose agar medium (supplied by Nissui Seiyaku Co. of Japan). The results shown in FIGS. 1A and 1B are obtained. In the figures, FIG. 1A indicates the result obtained from orange juice and FIG. 1B, from apple juice, respectively.

As apparent from the figures, the number of viable bacteria of *Alicyclobacillus acidoterrestris* decreased drastically with a lapse of time, leading to the conclusion that the effect of addition of alpha-type thionin of barley was confirmed.

What is claimed is:

1. A fruit-juice comprising a thionin.
2. The fruit juice of claim 1, wherein said thionin is selected from the group consisting of an alpha-type thionin and a beta-type thionin.
3. The fruit juice of claim 1, wherein said thionin is an alpha-type thionin in an amount ranging from 5 to 100 μg/mL.
4. The fruit juice of claim 1, wherein said thionin is a beta-type thionin in an amount ranging from 10 to 100 μg/mL.
5. The fruit juice of claim 1, wherein said fruit juice has been pasteurized.
6. The fruit juice of claim 1, wherein said fruit juice is apple juice.
7. The fruit juice of claim 1, wherein said fruit juice is orange juice.
8. The fruit juice of claim 1, wherein said thionin is a barley, oats, rye or wheat thionin.
9. A method for preserving a fruit juice or retarding the spoilage of a fruit juice comprising adding an amount of a thionin to said fruit juice effective to preserve said fruit juice or retard the spoilage of said fruit juice.
10. The method of claim 9, wherein said thionin is selected from the group consisting of an alpha-type thionin and a beta-type thionin.
11. The method of claim 9, wherein said fruit juice contains an acid-resistant or heat-resistant bacterium.
12. The method of claim 9, wherein said fruit juice contains *Alicyclobacillus acidoterrestris*.
13. A method of inhibiting the growth of an acid-resistant or heat-resistant bacteria belonging to the genus Alicyclobacillus, comprising contacting said bacterium with an effective amount of a thionin.
14. The method of claim 13, wherein said thionin is selected from the group consisting of alpha-type thionin and beta-type thionin.
15. The method of claim 13, wherein said thionin is a barley, oats, lye or wheat thionin.

* * * * *